United States Patent [19]

Sheen et al.

[11] Patent Number: 5,474,972
[45] Date of Patent: Dec. 12, 1995

[54] PESTICIDE AND FUNGICIDE COMPRISING AQUEOUS COPPER SILICATE

[76] Inventors: Ronald J. Sheen, 49 Eric Street, Cottesloe, Western Australia; Tom A. Langley, 71 Doonan Road, Nedlands, Western Australia, both of Australia

[21] Appl. No.: 211,621

[22] PCT Filed: Oct. 14, 1992

[86] PCT No.: PCT/AU92/00550

§ 371 Date: Jun. 14, 1994

§ 102(e) Date: Jun. 14, 1994

[87] PCT Pub. No.: WO93/07754

PCT Pub. Date: Apr. 29, 1993

[30] Foreign Application Priority Data

Oct. 17, 1991 [AU] Australia .................................. PK8968

[51] Int. Cl.⁶ ................................................... A01N 59/20
[52] U.S. Cl. .......................... 504/152; 504/153; 504/187; 424/630; 423/23; 423/27; 423/326
[58] Field of Search ...................... 504/153, 152, 504/187; 423/326, 23, 27; 424/630

[56] References Cited

U.S. PATENT DOCUMENTS

| | | | |
|---|---|---|---|
| 3,836,633 | 9/1974 | Beschke | 423/326 |
| 3,846,545 | 11/1974 | Hess et al. | 424/143 |
| 3,961,933 | 6/1976 | Kuyama et al. | 71/67 |
| 4,791,274 | 1/1989 | Miki et al. | 424/76.1 |

FOREIGN PATENT DOCUMENTS 0442228  8/1991  European Pat. Off. .

*Primary Examiner*—S. Mark Clardy
*Attorney, Agent, or Firm*—Birch, Stewart, Kolasch & Birch

[57] ABSTRACT

A method of producing a water soluble copper silicate by reacting a copper salt with an alkali silicate in an acidic solvent to produce an aqueous solution of acidified copper silicate capable of being used as a fungicide or pesticide.

15 Claims, No Drawings

PESTICIDE AND FUNGICIDE COMPRISING AQUEOUS COPPER SILICATE

This application has been filed under 35 USC 371 as a continuation of PCT/AU92/00550, filed Oct. 14, 1992.

BACKGROUND OF THE INVENTION

Field of the Invention

The present invention relates to a pesticide and fungicide, and more particularly relates to a slow release copper silicate product that may be used as a pesticide and fungicide, and also as an algaecide and insecticide.

Copper compounds have previously been used as pesticides, insecticides, algaecides and fungicides in a variety of liquid and solid forms. Use of copper compounds as fungicides is particularly common. However, known copper fungicides and pesticides are generally either phytotoxic, and are therefore fatal to young plants thus restricting the manners of use, or are only able to be provided as mainly insoluble powders which lose toxicity relatively quickly, are difficult to apply in some instances (being unable to be absorbed) and are only suitable for topical applications where the weather conditions (wind and rain) will not adversely disperse them.

Copper silicate is known for use as a fungicide and algaecide. However, copper silicate has traditionally only been used in solid form when precipitated from solution. This has caused copper silicate products to be seriously restricted in their commercial activities.

SUMMARY OF THE INVENTION

The object of the present invention is to provide a copper silicate product which overcomes, or at least partly alleviates, the above mentioned difficulties.

The present invention is characterised by an aqueous solution of acidified copper silicate for use primarily as a pesticide and fungicide. The invention is characterised by both the product and the method of producing such a product, the method comprising reacting a copper salt with an alkali silicate in an acidic solvent to produce the aqueous solution of acidified copper silicate.

DETAILED DESCRIPTION OF THE INVENTION

In a preferred form of the invention, the mixture of the copper salt and the alkali silicate is buffered in a pH range of about 2 to 6. This is to prevent the reaction of the components precipitating any insoluble compounds, such as silicic acid and/or copper silicate. In this respect, the solution should preferably be maintained in this pH range not only to maintain the solubility of the copper silicate, but also to produce a highly active copper silicate. The pH range is preferably carefully monitored as it is difficult to prevent the precipitation of copper silicate while also producing a product that is not unnecessarily excessively acidic. Indeed, the preferred range of pH for the solution is from 3 to 5, and this has been found to produce a highly active and highly soluble aqueous copper silicate product.

The copper salt of the invention is preferably a water soluble copper salt such as copper sulphate, while the alkali silicate is preferably sodium silicate. It will be noted however that, while being more expensive and less readily available commercially, copper acetate may also be utilised, while other copper salts could be copper bromide, chloride, fluoride, or nitrate. Furthermore, the alkali silicate could be potassium silicate. In this respect, the composition of the alkali silicate may be described by reference to the ratio of alkali oxide to silica, where the ratio $SiO_2:(Na \text{ or } K)_2O$ preferably covers a broad range such as from 3.75:1 to 1:2.

The copper silicate of the invention thus allows an aqueous solution to be applied to vegetation, or any type of structure or material, as a spray, thus giving improved coverage and penetration. In this respect, upon evaporation of the aqueous solvent, a largely insoluble acidic residue of amorphous hydrous silicate of copper remains. This residue adheres to the contacted surface, and is surface active to a variety of pests and fungi while remaining substantially non-phytotoxic. In this respect it will be understood that the term "non-phytotoxic" relates to the product being non-toxic to plant life other than fungi. Furthermore, when applied to timber or other types of porous materials the copper silicate may be absorbed into the material and upon drying remain impregnated within the material in a substantially insoluble form. The copper silicate may remain active for many months regardless of the prevailing weather conditions.

The buffer system preferably comprises a weak acid and its salts, such as acetic acid and sodium acetate or citric acid and sodium citrate. The preferred buffer system utilises acetic acid and sodium acetate in a ratio of between 1 to 5 and 5 to 1, and in a concentration of 0.01 to 10% w/w. In this preferred form, the buffer is created as a by-product of the reaction and provides a margin in maintaining the correct pH, which ideally is in the range of pH 3 to 5. However, it will be appreciated that there may not be a need for such a buffering system if the pH range can be otherwise carefully controlled by the use of an acid.

Thus, the present invention provides a copper silicate product for use as a pesticide or herbicide, the product being a stable, silicate rich, aqueous solution of acidified copper silicate having a pH in the range of 3 to 5. The present invention accordingly also provides a method of producing a copper silicate product for use as a fungicide or pesticide, the method comprising preparing separate batches of diluted copper sulphate, diluted sodium silicate and an acetic acid buffer, adding the acetic acid to the copper sulphate, followed by addition of the sodium silicate, to produce a stable, silicate rich, aqueous solution of acidified copper silicate having a pH in the range of 3 to 5.

It will also be appreciated that the copper silicate of the invention may be used in a solid form if required, utilising the ability of the aqueous solution to be absorbed or adsorbed by a solid carrier medium, with the subsequent evaporation or drying of the aqueous solvent leaving the largely insoluble acidic residue of amorphous hydrous copper silicate either interspersed within the carrier or topically applied thereto.

The product of the invention contains no complex organic chemicals and can be provided in an easy to use aqueous form which may be used as a fine spray for misting safely on trees or other plants and the like, or on any other type of surface such as on rocks, concrete paths, wood, bricks, or any surface as required. The product is substantially non-phytotoxic and has good tenacity, while also being capable of being absorbed into porous surfaces to provide an impregnated treated layer. This is particularly useful for use as a fungicide.

Thus, the problems that are often present in pesticides and fungicides in solid form may be avoided by the use of the present invention in its aqueous state. Pesticides in solid form are not only difficult to distribute such that they remain in place, but they provide only a limited ability to access awkward areas which are invariably the areas where pests accumulate. Furthermore, solid pesticides generally are unable to be used directly on plants, seedlings, trees, shrubs, berries or fruit and the like, and generally must be spatially distributed over large areas. Further still, it is not unusual for animals such as birds, dogs or cats, or even children, to be attracted to pesticides and fungicides in solid form which often presents a serious health risk both to animal life and human life due to the usually high toxicity of such compounds.

When the invention is used in its aqueous state, the residue which remains upon evaporation of the water solvent is largely insoluble and adheres very well to the contacted surface. It may be present in an active form for many months, and is safe for use with and around animals or children.

While testing has not yet been completed to determine the precise mechanism which occurs within pests such as snails, it is evident that upon contacting the residue the reaction with such pests is virtually immediate, and death follows some time thereafter. Snails in particular appear to produce large quantities of mucous and upon contact of the body of the snail with the residue of this pesticide, the snail dies apparently from dehydration which causes an overall system failure.

In order to better illustrate the present invention, an example of a preferred embodiment will now be described. However, it is to be understood that the generality of the invention as described above is not to be limited by the following description of the preferred embodiment.

The method for producing the aqueous solution of acidified copper silicate of the present invention is preferably conducted as a batch process. Firstly, sodium silicate having a preferred ratio of $SiO_2$ to $Na_2O$ in the range of 3.2 to 2, and having a pH range of 8 to 14 (or more preferably 11.6 to 12.7) is diluted with water. The range of concentration for the sodium silicate may be from 0.05 to 20% w/w, or more preferably is in the range 0.2 to 5.0% w/w.

At the same time, copper sulphate pentahydrate is dissolved in water and allowed to stand for between 8 and 24 hours, preferably overnight. The copper sulphate pentahydrate may have a concentration in the range of 0.1 to 25% w/w, but is more preferably in the range of 0.5 to 10% w/w.

Finally, acetic acid is also diluted with water. The concentration of the acetic acid may be in the range of 0.01 to 10% w/w, but is more preferably in the range of 0.05 to 2.0% w/w.

It will be appreciated by a person skilled in the art that the concentrations described may be altered, provided that the approximate ratios of components remain the same. Furthermore, while it is preferred to use an excess amount of acetic acid, a solution that is too acidic will most likely be toxic or corrosive to the plant or surface to which it is applied and thus should be avoided.

After preparation of the components referred to above, the acetic acid is added to the dissolved copper sulphate solution, with stirring. The subsequently obtained mixture is then added to the sodium silicate solution, again with stirring. The total mixture is then diluted with water. If required, dyes and or wetting agents may be added at this stage, and the total mixture may be subjected to a final filtration, and is packaged as needed.

It will also be appreciated that the method of producing the product may be carried out as a continuous process with some modification. In this respect, bulk solutions of copper sulphate, acetic acid and sodium silicate may be provided so as to be treated and mixed as above, provided the proportions of each are maintained, using the necessary mixing, stirring, monitoring and flow control apparatus as needed. In this respect, the presence of impurities within the raw materials may provide a seed for precipitation or crystallisation at later stages, which could result in the production of an unstable product. As the method of the invention aims at avoiding precipitation of copper silicate in particular, filtration may also be utilised as necessary.

In the method of the invention, it is believed that the sodium of the sodium silicate is neutralised by the excess acetic acid and creates the previously described buffer system. It is also believed that the copper reacts with the excess silicate to form copper silicate which is maintained in solution by the buffer. Other chemical species present may be sodium sulphate and sulphuric acid. Furthermore, while the active ingredient in the subsequently obtained residue is acidic copper silicate, other compounds may coexist, such as copper sulphate, copper acetate, sodium silicate, sodium acetate, acetic acid, silicic acid, sodium silicate and sulphuric acid, or any such combinations.

Finally, and as indicated above, the product of the invention may be converted for use in a solid form as desired for a particular application. For example, the product may be sprayed onto an absorbent granule such as attapulgite or montmorillonite clays, although a variety of other carriers such as expanded perlite, exfoliated vermiculite and calcium carbonate granules could be used. In this respect, it will be appreciated that the type of carrier used will be substantially dependent on the environment in which the product will be used and also the particular type of use required.

After spraying the product onto a chosen carrier, the carrier grannules may be dried, leaving the copper silicate residue upon and within the granules. The granule size is preferably in the range of 0.1 to 5 mm, although other size ranges may be appropriate and may be used if needed. In this respect, it is also envisaged that the product may be used with powders, whether they be adsorbent or absorbent, such as talc powder (adsorbent) or kaolin clay and diatomite (absorbent). Of course, when using the adsorbent, the residue after drying remains only on the outside of the particles.

Those skilled in the art will also appreciate that there may be other variations and modifications of the method and product described herein which are also within the scope of the present invention.

What is claimed is:

1. A method of producing a copper silicate product, comprising reacting a copper salt with an alkali silicate in an acidic solvent to produce an aqueous solution of acidified copper silicate capable of being used as a fungicide or pesticide.

2. A method according to claim 1 wherein the acidic solvent buffers the mixture of copper salt and alkali silicate such that the acidified copper silicate has a pH in the range of 2 to 6.

3. The method according to claim 2 wherein the pH is in the range of 3 to 5.

4. The method according to any one of claims 1 to 3 wherein the acidic solvent comprises acetic acid and sodium acetate.

5. The method according to claim 4 wherein the acetic acid and sodium acetate are in a ratio of between 1:5 and 5:1 and in a concentration of 0.01 to 10% w/w.

6. The method according to claim 1 wherein the copper salt is copper sulphate.

7. The method according to claim 6 wherein the copper sulphate is copper sulphate pentahydrate and is present in an amount in the range of 0.1 to 25% w/w.

8. The method according to claim 1 wherein the alkali silicate is sodium silicate.

9. The method according to claim 8 wherein the sodium silicate has a ratio of $SiO_2$ to $Na_2O$ of from 3.75:1 to 1:2, and is present in an amount in the range of 0.05 to 20% w/w.

10. The method according to claim 1 wherein the copper salt is copper sulphate pentahydrate in an amount in the range of 0.5 to 10% w/w, the alkali silicate is sodium silicate having a ratio of $SiO_2$ to $Na_2O$ in the range of 2.5:1.5 to 3.5:2.5, a pH range of 10 to 14 and in an amount in the range of 0.2 to 5.0% w/w, and the acidic solvent is an acetic acid/sodium acetate buffer system having acetic acid in an amount in the range of 0.05 to 2.0% w/w.

11. The method according to claim 1 wherein the copper salt, the alkali silicate and the acidic solvent are each separately diluted with water and at least the copper salt is allowed to stand for between 8 and 24 hours, the acidic solvent is then added to the diluted copper salt with stirring, and the alkali silicate solution added thereafter with stirring, following which the mixture is diluted with water.

12. A method of producing a copper silicate product for use as a fungicide or pesticide, the method comprising preparing in separate batches (1) diluted copper sulphate, (2) diluted sodium silicate, and (3) an acetic acid buffer, adding the acetic acid buffer to the diluted copper sulphate, then adding the diluted sodium silicate to this mixture, to produce a stable, silicate rich, aqueous solution of acidified copper silicate having a pH in the range of 3 to 5.

13. A copper silicate product produced by the method of claim 1.

14. A copper silicate product produced by the method of claim 12.

15. A copper silicate product for use as a pesticide or herbicide, said product being a stable, silicate rich, aqueous solution of acidified copper silicate having a pH in the range of 3 to 5.

\* \* \* \* \*